United States Patent
Sawa

(10) Patent No.: US 6,306,856 B1
(45) Date of Patent: Oct. 23, 2001

(54) METHOD FOR SOLUBILIZING PYRIDONECARBOXYLIC ACID, SOLUBILIZER THEREFOR, AQUEOUS SOLUTION PREPARATION CONTAINING PYRIDONECARBOXYLIC ACID AND PROCESS FOR PRODUCING THE SAME

(75) Inventor: Shirou Sawa, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/554,660

(22) PCT Filed: Sep. 13, 1999

(86) PCT No.: PCT/JP99/04992

§ 371 Date: May 18, 2000

§ 102(e) Date: May 18, 2000

(87) PCT Pub. No.: WO00/16774

PCT Pub. Date: Mar. 30, 2000

(30) Foreign Application Priority Data

Sep. 13, 1999 (JP) .................................................. 10-265523

(51) Int. Cl.$^7$ ..................................................... A61K 31/50
(52) U.S. Cl. ...................................... 514/252.02; 514/248
(58) Field of Search ................................ 514/248, 252.02

(56) References Cited

FOREIGN PATENT DOCUMENTS

| | | |
|---|---|---|
| 60-994910 | 5/1985 | (JP) . |
| 61-180771 | 8/1986 | (JP) . |
| 62-149671 | 7/1987 | (JP) . |
| 63-288626 | 8/1988 | (JP) . |
| 2-83318 | 3/1990 | (JP) . |
| 3-109326 | 5/1991 | (JP) . |
| 9-216820 | 8/1997 | (JP) . |
| 10-25255 | 1/1998 | (JP) . |

*Primary Examiner*—Zohreh Fay
(74) *Attorney, Agent, or Firm*—Wenderoth, Lind & Ponack, L.L.P.

(57) ABSTRACT

The present invention relates to a method for solubilizing pyridonecarboxylic acid or a pharmacologically acceptable salt thereof, which includes incorporating glycyrrhizic acid or a salt thereof and pyridonecarboxylic acid or a pharmacologically acceptable salt thereof, a solubilizer therefor, an aqueous solution containing the solubilized pyridonecarboxylic acid or a pharmacologically acceptable salt thereof, and a method of producing the aqueous solution. According to the solubilizing method of the present invention, the solubility of pyridonecarboxylic acid compound and salts thereof near physiological pH can be increased. Therefore, these compounds can be prepared into an aqueous solution to be applied as an eye drop, a nasal drop and an ear drop.

8 Claims, No Drawings

METHOD FOR SOLUBILIZING PYRIDONECARBOXYLIC ACID, SOLUBILIZER THEREFOR, AQUEOUS SOLUTION PREPARATION CONTAINING PYRIDONECARBOXYLIC ACID AND PROCESS FOR PRODUCING THE SAME

This application is a 371 application of PCT/JP99/04992 filed Sep. 13, 1999.

TECHNICAL FIELD OF THE INVENTION

The present invention relates to a method for solubilizing pyridonecarboxylic acid, which is an amphoteric compound and which has an antibacterial activity, and a pharmacologically acceptable salt thereof, a solubilizer therefor, an aqueous solution preparation containing solubilized pyridonecarboxylic acid, and a production method thereof.

BACKGROUND OF THE INVENTION

Pyridonecarboxylic acid and pharmacologically acceptable salts thereof are superior synthetic antibacterial agents. However, since pyridonecarboxylic acid has carboxylic acid and the dihydropyridine skeleton in a molecule, forming a zwitterion, it shows low solubility in water at a physiological pH, i.e., neutral range. This imposes a problem that an aqueous solution containing pyridonecarboxylic acid or a pharmacologically acceptable salt thereof cannot be formulated into a pharmaceutical preparation having a near neutral pH.

Hardly soluble pyridonecarboxylic acid and a pharmacologically acceptable salt thereof have been conventionally solubilized by, for example, adding an inorganic acid to pyridonecarboxylic lactate (JP-A-60-94910), or adding an excess base to pyridonecarboxylic acid (JP-A-61-180771), or adding a metal compound comprising aluminum, magnesium or zinc to pyridonecarboxylic acid or a salt thereof (JP-A-63-188626). The aqueous solutions thus obtained show changes in pH, which is caused by the solubilizer added, and the toxicity of the solubilizer itself which may cause a local irritation and the like. In addition, the absorption into the living body may decrease due to an interaction between the solubilizer and pyridonecarboxylic acid.

Thus, there has not been provided an aqueous solution containing solubilized pyridonecarboxylic acid, which is safe and useful at a physiological pH, i.e., about neutral pH (pH 6–8).

DISCLOSURE OF THE INVENTION

It is an object of the present invention to provide a method for solubilizing pyridonecarboxylic acid and a pharmacologically acceptable salt thereof.

Another object of the present invention is to provide a solubilizer for pyridonecarboxylic acid and a pharmacologically acceptable salt thereof.

A yet another object of the present invention is to provide an aqueous solution having an improved solubility of pyridonecarboxylic acid and a pharmacologically acceptable salt thereof.

A further object of the present invention is to provide a method for producing an aqueous solution comprising pyridonecarboxylic acid or a pharmacologically acceptable salt thereof.

The present inventor has conducted intensive studies in an attempt to achieve the above-mentioned objects, and found that glycyrrhizic acid and a salt thereof can solubilize pyridonecarboxylic acid and a pharmacologically acceptable salt thereof in water at a physiological pH, which resulted in the completion of the present invention.

Thus, the present invention provides the following.

(1) A method for solubilizing pyridonecarboxylic acid or a pharmacologically acceptable salt thereof, comprising incorporating glycyrrhizic acid or a salt thereof and pyridonecarboxylic acid or a pharmacologically acceptable salt thereof.

(2) The method for solubilizing pyridonecarboxylic acid or a pharmacologically acceptable salt thereof according to (1) above, which comprises adding pyridonecarboxylic acid or a pharmacologically acceptable salt thereof to water, adjusting pH to not more than 3, adding glycyrrhizic acid or a salt thereof and adjusting pH of this aqueous solution to 3.5–8.5.

(3) The method for solubilizing pyridonecarboxylic acid or a pharmacologically acceptable salt thereof according to (1) above, wherein the pyridonecarboxylic acid is a compound of the formula (I):

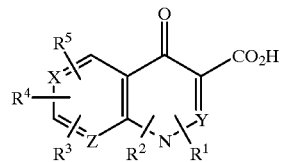

wherein X, Y and Z may be the same or different and each is nitrogen atom or optionally substituted CH, $R^1$, $R^2$, $R^3$, $R^4$ and $R^5$ may be the same or different and each is hydrogen atom, halogen, carboxyl group, optionally substituted lower alkyl, optionally substituted cycloalkyl, optionally substituted acyl, optionally substituted aryl or optionally substituted heterocyclic group, or at least two members selected from $R^1$, $R^2$, $R^3$, $R^4$ and $R^5$ in combination form an optionally substituted 4- to 7-membered ring via or not via a hetero atom.

(4) The method for solubilizing pyridonecarboxylic acid or a pharmacologically acceptable salt thereof according to (1) above, wherein the pyridonecarboxylic acid is a member selected from the group consisting of lomefloxacin, norfloxacin, enoxacin, ofloxacin, ciprofloxacin, tosufloxacin, fleroxacin, cinoxacin, levofloxacin and sparfloxacin.

(5) A solubilizer for pyridonecarboxylic acid or a pharmacologically acceptable salt thereof, which comprises glycyrrhizic acid or a salt thereof as an active ingredient.

(6) An aqueous solution comprising pyridonecarboxylic acid or a pharmacologically acceptable salt thereof, and glycyrrhizic acid or a salt thereof.

(7) The aqueous solution of (6) above, which is in the form of an eye drop, nasal drop or ear drop.

(8) A method for producing an aqueous solution comprising pyridonecarboxylic acid or a pharmacologically acceptable salt thereof, which comprises incorporating glycyrrhizic acid or a salt thereof and pyridonecarboxylic acid or a pharmacologically acceptable salt thereof.

(9) The method for producing an aqueous solution comprising pyridonecarboxylic acid or a pharmacologically acceptable salt thereof according to (8) above, which comprises adding pyridonecarboxylic acid or a pharmacologically acceptable salt thereof to water, adjusting pH to not more than 3, adding glycyrrhizic acid or a salt thereof, and adjusting pH of this aqueous solution to 3.5–8.5.

DETAILED DESCRIPTION OF THE INVENTION

The pyridonecarboxylic acid and a pharmacologically acceptable salt thereof, which are amphoteric compounds and which have an antibacterial activity, are solubilized by incorporating these compounds and a solubilizing agent containing glycyrrhizic acid or a salt thereof as an active ingredient.

For example, pyridonecarboxylic acid or a pharmacologically acceptable salt thereof is added to water, the mixture is adjusted to pH 3 or below with an acid such as hydrochloric acid, phosphoric acid, acetic acid and the like, glycyrrhizic acid or a salt thereof is added thereto, and this aqueous solution is adjusted to pH 3.5–8.5, preferably 6–8, with an alkali such as sodium hydroxide, potassium hydroxide, monoethanolamine and tromethamine. The pyridonecarboxylic acid and a pharmacologically acceptable salt thereof are generally subjected to the above-mentioned solubilization in water at around room temperature.

The pyridonecarboxylic acid is free of any particular imitation as long as it is a compound having a carboxyl group at the 3-position of the pyridine skeleton or pyridazine skeleton and an oxo group at the 4-position thereof.

The pyridonecarboxylic acid capable of exerting a significant effect as a solubilization target in the present invention has a solubility in water, which corresponds to the solubility of from "somewhat insoluble" to "sparingly soluble" in the solubility test as defined in Japan Pharmacopoeia, 13th Edition, Explanation (1996), Hirokawashoten, Tokyo, p. A-51, General Notices 23, Description, or from "sparingly soluble" to "practically insoluble" as defined in International Pharmacopoeia III.

The pyridonecarboxylic acid to be preferably used has the following formula (I):

(I)

wherein X, Y and Z may be the same or different and each is nitrogen atom or optionally substituted CH, $R^1$, $R^2$, $R^3$, $R^4$ and $R^5$ may be the same or different and each is hydrogen atom, halogen, carboxylic group, optionally substituted lower alkyl, optionally substituted cycloalkyl, optionally substituted acyl, optionally substituted aryl or optionally substituted heterocyclic group, or at least two members selected from $R^1$, $R^2$, $R^3$, $R^4$ and $R^5$ in combination form an optionally substituted 4- to 7-membered ring via or not via a hetero atom.

"Halogen" is exemplified by fluorine, chlorine, bromine, iodine and the like.

The lower alkyl moiety of the "optionally substituted lower alkyl" preferably has 1 to 6 carbon atoms, and is exemplified by a linear or branched one, such as methyl, ethyl, propyl, isopropyl, isobutyl, tert-butyl, pentyl, isopentyl, neopentyl, tert-pentyl, hexyl, isohexyl, neohexyl and the like.

Examples of the substituent of lower alkyl include halogen (e.g., fluorine, chlorine, bromine and iodine) and the like, with preference given to fluorine, chlorine and bromine.

The cycloalkyl moiety of the "optionally substituted cycloalkyl" preferably has 3 to 9 carbon atoms, and is exemplified by cyclopropyl, cyclobutyl, cyclopentyl, cyclohexyl, cycloheptyl and the like.

The substituents of cycloalkyl include lower alkyl (e.g., those having 1 to 4 carbon atoms such as methyl, ethyl, propyl and isopropyl), halogen (e.g., fluorine, chlorine, bromine and iodine) and the like.

The acyl moiety of the "optionally substituted acyl" may be, for example, alkanoyl such as formyl, acetyl, propionyl, butyryl, isobutyryl, valeryl and the like, and aromatic acyl such as benzoyl, naphthoyl, toluoyl, salicyloyl and the like.

The above-mentioned acyl may be substituted by substituents which may be the same or different, such as lower alkyl (e.g., those having 1 to 4 carbon atoms, such as methyl, ethyl, propyl etc.);

lower alkoxy (e.g., those having 1 to 4 carbon atoms, such as methoxy, ethoxy, propoxy etc.);

lower alkylthio (e.g., those having 1 to 4 carbon atoms, such as methylthio, ethylthio etc.);

lower alkylamino (e.g., those having 1 to 4 carbon atoms, such as methylamino, ethylamino, propylamino and the like);

cyclo(lower)alkyl such as cyclo($C_3$–$C_6$)alkyl (e.g., cyclopentyl, cyclohexyl etc.);

cyclo(lower)alkenyl such as cyclo($C_3$–$C_6$)alkenyl (e.g., cyclohexenyl, cyclohexadienyl etc.);

halogen (e.g., fluorine, chlorine, bromine, iodine);

amino; protected amino; hydroxy; protected hydroxy; cyano; nitro; carboxy; protected carboxy; sulfo; sulfamoyl; imino; oxo;

amino(lower)alkyl (e.g., those having 1 to 4 carbon atoms, such as aminomethyl, aminoethyl etc.); carbamoyloxy; hydroxy(lower)alkyl (e.g., those having 1 to 4 carbon atoms, such as hydroxymethyl, 1- or 2-hydroxyethyl, 1- or 2- or 3-hydroxypropyl etc.); and the like.

The aryl moiety of the "optionally substituted aryl" preferably has not more than 14 carbon atoms. Examples thereof include phenyl, naphthyl and the like, with particular preference given to naphthyl.

The heterocyclic moiety of the "optionally substituted heterocyclic group" preferably has not more than 14 carbon atoms. In addition, it has at least one hetero atom besides carbon atom, which is selected from nitrogen atom, sulfur atom and oxygen atom, as an atom constituting the ring. The heterocyclic group encompasses saturated or unsaturated heteromonocyclic and heteropolycyclic groups.

Preferable heterocyclic groups are the following:

3- to 6-membered unsaturated heteromonocyclic group having 1 to 4nitrogen atoms, such as pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl etc.), tetrazolyl (e.g., 1H-tetrazolyl, 2H-tetrazolyl etc.), triazinyl (e.g., 1,2,4-triazinyl etc.), and the like;

3- to 7-membered saturated heteromonocyclic group having 1 to 4 nitrogen atoms, such as pyrrolidinyl, imidazolidinyl, piperidinyl, piperazinyl, homopiperazinyl and the like;

saturated heteropolycyclic group having 1 to 4 nitrogen atoms, such as quinuclidinyl and the like;

unsaturated heteropolycyclic group having 1 to 5 nitrogen atoms, such as indolyl, isoindolyl, 3H-indolyl, indolizinyl, benzimidazolyl, quinolyl, isoquinolyl, indazolyl, phthalazinyl, naphthyridinyl, quinoxalinyl, quinazolinyl, cinnolinyl, benzotriazolyl, tetrazolopyridazinyl (e.g., tetrazolo[1,5-b]pyridazinyl etc.), pteridinyl, carbazolyl, phenanthridinyl, acridinyl, perimidinyl, and the like;

3- to 6-membered unsaturated heteromonocyclic group having 1 to 3 nitrogen atoms and 1 or 2 oxygen atoms, such as oxazolyl, isoxazolyl, oxadiazolyl (e.g., 1,2,4-oxadiazolyl, 1,3,4-oxadiazolyl, 1,2,5-oxadiazolyl etc.), and the like;

3- to 6-membered saturated heteromonocyclic group having 1 to 3 nitrogen atoms and 1 or 2 oxygen, atoms, such as morpholinyl, sydnonyl, and the like;

unsaturated condensed heterocyclic group having 1 to 3 nitrogen atoms and 1 or 2 oxygen atoms, such as benzofurazanyl, benzoxazolyl, benzoxazinyl, benzoxadiazolyl, and the like;

3- to 6-membered unsaturated condensed heterocyclic group having 1 to 3 nitrogen atoms and 1 or 2 sulfur atoms, such as thiazolyl, isothiazolyl, thiadiazolyl (e.g., 1,2,4-thiadiazolyl, 1,3,4-thiadiazolyl, 1,2,5-thiadiazolyl etc.), and the like;

3- to 6-membered saturated heteromonocyclic group having 1 to 3 nitrogen atoms and 1 or 2 sulfur atoms, such as thiazolidinyl and the like;

unsaturated condensed heterocyclic group having 1 to 3 nitrogen atoms and 1 or 2 sulfur atoms, such as benzothiazolyl, benzothiadiazolyl, and the like;

3- to 6-membered unsaturated heteromonocyclic group having 1 oxygen atom, such as furyl, pyranyl and the like;

3- to 6-membered unsaturated heteromonocyclic group having 1 or 2 sulfur atoms, such as thienyl, dihydrothienyl, and the like;

unsaturated condensed heterocyclic group having 1 or 2 sulfur atoms, such as benzothienyl etc.; and the like.

The above-mentioned "heterocyclic group" and "aryl" are optionally substituted by one or more substituents. Examples of the substituent include hydroxyl, halogen, alkyl optionally substituted by halogen, aralkyl, aliphatic carboxylic acid residue, aromatic carboxylic acid residue, acyloxy, aroyloxy, alkoxy, aryloxy, aliphatic alcohol residue, aromatic alcohol residue, aliphatic aldehyde, aromatic aldehyde, amino, aliphatic amino, aromatic amino and the like. The substituent of heterocyclic group may be aryl.

The "hetero atom" is exemplified by nitrogen, oxygen and sulfur. The number of hetero atom is preferably 2.

The 4- to 7-membered ring moiety of the "optionally substituted 4- to 7-membered ring" is cycloalkyl and heterocyclic group, preferably heterocyclic group.

Preferable heterocyclic group includes thienyl, furyl, pyrrolyl, imidazolyl, pyrazolyl, thiazolyl, isothiazolyl, oxazolyl, isoxazolyl, oxadiazolyl, thiadiazolyl, triazolyl, pyridyl, pyrazinyl, pyrimidinyl, pyridazinyl, triazinyl, dithiazolyl, dioxolanyl, dithiolyl, pyrrolidinyl, thiadiazinyl, dithiadiazinyl, morpholinyl, oxazinyl, thiazinyl, piperazinyl, piperidinyl, pyranyl, thiopyranyl and the like.

The substituent for the 4- to 7-membered ring is exemplified by lower alkyl (e.g., those having 1 to 4 carbon atoms, such as methyl, ethyl, propyl, isopropyl etc.) and the like.

$R^1$, $R^2$, $R^3$, $R^4$ and $R^5$ can be a substituent of any ring of the condensed ring in the formula (I).

With regard to the "optionally substituted CH", by optionally substituted is meant that the group may be substituted by any of $R^1$ to $R^5$.

When two or more of X, Y and Z are nitrogen atoms at the same time, the total number of the substituents may be 4 or less.

Examples of the pyridonecarboxylic acid include enoxacin: [1-ethyl-6-fluoro-1,4-dihydro-4-oxo-7-(1-piperazinyl)-1,8-naphthyridine-3-carboxylic acid], ofloxacin: [(±)-9-fluoro-2,3-dihydro-3-methyl-10-(4-methyl-1-piperazinyl)-7-oxo-7H-pyrido[1,2,3-de]-1,4-benzoxazine-6-carboxylic acid], cinoxacin: [1-ethyl-1,4-dihydro-4-oxo[1,3]dioxolo[4,5-g]cinnoline-3-carboxylic acid], ciprofloxacin: [1-cyclopropyl-6-fluoro-1,4-dihydro-4-oxo-7-(1-piperazinyl)-3-quinolinecarboxylic acid], sparfloxacin: [5-amino-1-cyclopropyl-7-(cis-3,5-dimethyl-1-piperazinyl)-6,8-difluoro-1,4-dihydro-4-oxo-3-quinolinecarboxylic acid], tosufloxacin: [(±)-7-(3-amino-1-pyrrolidinyl)-1-(2,4-difluorophenyl)-6-fluoro-1,4-dihydro-4-oxo-1,8-naphthyridine-3-carboxylic acid], norfloxacin: [1-ethyl-6-fluoro-1,4-dihydro-4-oxo-7-(1-piperazinyl)-3-quinolinecarboxylic acid], fleroxacin: [6,8-difluoro-1-(2-fluoroethyl)-1,4-dihydro-7-(4-methyl-1-piperazinyl)-4-oxo-3-quinolinecarboxylic acid], levofloxacin: [(S)-(−)-9-fluoro-2,3-dihydro-3-methyl-10-(4-methyl-1-piperazinyl)-7-oxo-7H-pyrido[1,2,3-de]-1,4-benzoxazine-6-carboxylic acid), lomefloxacin: [1-ethyl-6,8-difluoro-1,4-dihydro-7-(3-methyl-1-piperazinyl)-4-oxo-3-quinolinecarboxylic acid], 5,8-dihydro-8-ethyl-2-(1-piperazinyl)-5-oxopyrido[2,3-d]pyrimidinecarboxylic acid, 7-(3-amino-1-pyrrolidinyl)-1-ethyl-6-fluoro-1,4-dihydro-4-oxo-1,8-naphthyridine-3-carboxylic acid, 7-(3-amino-1-pyrrolidinyl)-1-cyclopropyl-6-fluoro-1,4-dihydro-4-oxo-1,8-naphthyridine-3-carboxylic acid, 1-cyclopropyl-6-fluoro-7-(3-methylamino-1-pyrrolidinyl)-1,4-dihydro-4-oxo-1,8-naphthyridine-3-carboxylic acid, 7-(3-amino-3-methyl-1-pyrrolidinyl)-1-cyclopropyl-6-fluoro-1,4-dihydro-4-oxo-1,8-naphthyridine-3-carboxylic acid and the like, and pharmacologically acceptable salts thereof.

The pharmacologically acceptable salts of pyridonecarboxylic acid include, for example, acid addition salts with inorganic acids such as hydrochloric acid, sulfuric acid, phosphoric acid etc., with organic acids such as acetic acid, lactic acid, succinic acid, methanesulfonic acid, maleic acid, malonic acid, gluconic acid, p-toluenesulfonic acid etc., or with amino acids such as aspartic acid, glutamic acid etc.; alkali metal salts such as sodium salt, potassium salt etc.; and the like.

The salt of glycyrrhizic acid may be alkali metal salt, such as sodium salt, potassium salt etc., alkaline earth metal salt, such as magnesium salt, calcium salt etc., and the like.

The amount of glycyrrhizic acid to be added to pyridonecarboxylic acid or a pharmacologically acceptable salt thereof is preferably about 0.001–100 parts by weight, more preferably about 0.001–10 parts by weight, per part by weight of pyridonecarboxylic acid or a pharmacologically acceptable salt thereof.

The solubilizer for pyridonecarboxylic acid and a pharmacologically acceptable salt thereof contains glycyrrhizic acid or a salt thereof as an active ingredient.

The solvent to be used for the aqueous solution of the present invention is purified water, and distilled water for injection is particularly preferable. The concentration of pyridonecarboxylic acid in the aqueous solution is strikingly increased to generally not less than 0.5 (w/v) %, preferably not less than 5.0 (w/v) %, particularly preferably 10 (w/v) %, by the addition of glycyrrhizic acid or a salt thereof.

This aqueous solution may contain various additives as appropriate, such as buffer, isotonication agent, solubilizer, antiseptic, thickener, chelating agent, aromatic and the like.

Examples of the buffer include phosphate buffer, borate buffer, citrate buffer, tartrate buffer, acetate buffer, amino acid and the like.

Examples of the isotonication agent include sugars such as sorbitol, glucose, mannitol etc., polyhydric alcohols such as glycerol, propylene glycol etc., salts such as sodium chloride etc., and the like.

Examples of the solubilizer include nonionic surfactants such as polyoxyethylenesorbitan monooleate, polyoxyethyleneoxystearic acid triglyceride, polyethylene glycol, polyoxyethylene hydrogenated castor oil etc., and the like.

Examples of the antiseptic include quaternary ammonium salts such as benzalkonium chloride, benzethonium chloride, cetylpyridinium chloride etc., p-hydroxybenzoates such as methyl p-hydroxybenzoate, ethyl p-hydroxybenzoate, propyl p-hydroxybenzoate, butyl p-hydroxybenzoate etc., benzyl alcohol, phenylethyl alcohol, sorbic acid, salts thereof, thimerosal, chlorobutanol, sodium dehydroacetate and the like.

Examples of the thickener include polyvinylpyrrolidone, hydroxyethylcellulose, hydroxypropylcellulose, methylcellulose, hydroxypropylmethylcellulose, carboxymethylcellulose, salts thereof and the like.

Examples of the chelating agent include sodium edetate, citric acid, and the like.

Examples of the aromatic include 1-menthol, borneol, camphor, eucalyptus oil and the like.

The aqueous solution of the present invention is preferably used as an eye drop, nasal drop or ear drop. When it is used as an eye drop, its pH is generally adjusted to about 3.5–8.5, preferably about 6–8; when it is used as a nasal drop, its pH is generally adjusted to about 3.5–8.5, preferably about 6–8; and when it is used as an ear drop, its pH is generally adjusted to about 3.5–8.5, preferably about 6–8.

The method for producing the aqueous solution of the present invention is similar to the solubilization of pyridonecarboxylic acid and a pharmacologically acceptable salt thereof mentioned earlier. The above-mentioned various additives can be added during a suitable step.

When the aqueous solution of the present invention is used as an eye drop, for example, the dose thereof need only be sufficient to effectively suppress inflammation in the eye, and may vary according to symptoms, the kind of inflammation, the patients in need of the liquid preparation, the kind of animal, and the like. A typical dose is 20–200 μg/dose, preferably 50–100 μg/dose, which may be administered 1 to 12 times a day.

The present invention is described in more detail by way of Experimental Example and Example.

Experimental Example
Effect of Glycyyrrhizic Acid and a Salt Thereof on the Solubility of Pyridonecarboxylic Acid To a 1.6% aqueous boric acid solution (100 ml) containing 0.1% dipotassium glycyrrhizinate was added an excess lomefloxacin hydrochloride, and the pH was adjusted to 7 with sodium hydroxide. To an aqueous phosphoric acid solution (isotonized with sodium chloride) containing 0.1% dipotassium glycyrrhizinate was added an excess ofloxacin, and the pH was adjusted to 7 with sodium hydroxide. These solutions were shaken at 25° C. for about one week and filtered through a 0.45 μm membrane filter. The contents of lomefloxacin hydrochloride and ofloxacin were measured by high performance liquid chromatography. The results are shown in Table 1.

TABLE 1

| Drug name | Solubility (mg/ml) | |
|---|---|---|
| | without addition | Incorporating 0.1% dipotassium glycyrrhizinate |
| lomefloxacin hydrochloride | 1.10 (n = 2) | 2.98 (n = 2) |
| ofloxacin | 5.16 (n = 1) | 9.42 (n = 1) | n: number of sample

As is evident from Table 1, the incorporation of 0.1% dipotassium glycyrrhizinate resulted in about 3 times higher solubility of lomefloxacin hydrochloride and about 2 times higher solubility of ofloxacin, demonstrating a striking solubilizing effect afforded by 0.1% dipotassium glycyrrhizinate.

EXAMPLE

An eye drop was prepared according to the following recipe.

Lomefloxacin hydrochloride (0.3 g) was added to water (100 ml) and the mixture was adjusted to pH 3 with hydrochloric acid to dissolve lomefloxacin hydrochloride. Thereto was added dipotassium glycyrrhizinate (0.1 g) and the mixture was adjusted to pH 7 with sodium hydroxide.

This solution was free of precipitation of crystals after storage at room temperature for 3 days. When dipotassium glycyrrhizinate was not added, crystals precipitated after storage at room temperature for about 1 hr to 1 day.

| | |
|---|---|
| lomefloxacin hydrochloride | 0.3 g |
| dipotassium glycyrrhizinate | 0.1 g |
| boric acid | 1.6 g |
| sodium hydroxide | appropriate amount |
| hydrochloric acid | appropriate amount |
| sterile purified water | appropriate amount |
| total amount | 100 ml |
| pH | 7.0 |

INDUSTRIAL APPLICABILITY

According to the solubilizing method of the present invention, the solubility of pyridonecarboxylic acid compound and salts thereof at near physiological pH can be increased. Therefore, these compounds can be prepared into an aqueous solution to be applied as an eye drop, a nasal drop and an ear drop.

This application is based on application No. 265523/1998 filed in Japan, the contents of which are incorporated hereinto by reference.

What is claimed is:

1. A method for solubilizing pyridonecarboxylic acid or a pharmacologically acceptable salt thereof, comprising incorporating glycyrrhizic acid or a salt thereof and pyridonecarboxylic acid or a pharmacologically acceptable salt thereof.

2. The method for solubilizing pyridonecarboxylic acid or a pharmacologically acceptable salt thereof according to claim 1, which comprises adding pyridonecarboxylic acid or a pharmacologically acceptable salt thereof to water, adjusting pH to not more than 3, adding glcyrrhizic acid or a salt thereof and adjusting pH of the aqueous solution to 3.5–8.5.

3. The method for solubilizing pyridonecarboxylic acid or a pharmacologically acceptable salt thereof according to claim 1, wherein the pyridonecarboxylic acid is a compound of the formula (I):

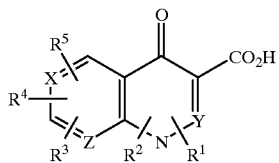

(I)

wherein X, Y and Z may be the same or different and each is nitrogen atom or optionally substituted CH, and $R^1$, $R^2$, $R^3$, $R^4$ and $R^5$ may be the same or different and each is hydrogen atom, halogen, carboxyl group, optionally substituted lower alkyl, optionally substituted cycloalkyl, optionally substituted acyl, optionally substituted aryl or optionally substituted heterocyclic group, or at least two members selected from $R^1$, $R^2$, $R^3$, $R^4$ and $R^5$ in combination form an optionally substituted 4- to 7-membered ring via or not via a hetero atom.

4. The method for solubilizing pyridonecarboxylic acid or a pharmacologically acceptable salt thereof according to claim 1, wherein the pyridonecarboxylic acid is a compound selected from the group consisting of lomefloxacin, norfloxacin, enoxacin, ofloxacin, ciprofloxacin, tosufloxacin, fleroxacin, cinoxacin, levofloxacin and sparfloxacin.

5. An aqueous solution comprising pyridonecarboxylic acid or a pharmacologically acceptable salt thereof, and glycyrrhizic acid or a salt thereof.

6. The aqueous solution of claim 5, which is in the form of an eye drop, nasal drop or ear drop.

7. A method for producing an aqueous solution comprising pyridonecarboxylic acid or a pharmacologically acceptable salt thereof, which comprises incorporating glycyrrhizic acid or a salt thereof and pyridonecarboxylic acid or a pharmacologically acceptable salt thereof.

8. The method for producing an aqueous solution comprising pyridonecarboxylic acid or a pharmacologically acceptable salt thereof according to claim 7, which comprises adding pyridonecarboxylic acid or a pharmacologically acceptable salt thereof to water, adjusting pH to not more than 3, adding glycyrrhizic acid or a salt thereof, and adjusting pH of the aqueous solution to 3.5–8.5.

* * * * *

UNITED STATES PATENT AND TRADEMARK OFFICE
CERTIFICATE OF CORRECTION

PATENT NO.  : 6,306,856 B1
DATED       : October 23, 2001
INVENTOR(S) : Shirou Sawa It is certified that error appears in the above-identified patent and that said Letters Patent is hereby corrected as shown below:

<u>Title page,</u>
Item [30], change "Sep. 13, 1999" to -- Sep. 18, 1998 --.

<u>Column 3,</u>
Line 26, change "imitation" to -- limitation --.

<u>Column 5,</u>
Line 15, change "oxygen, atoms" to -- oxygen atoms --.

<u>Column 7,</u>
Line 54, change "Glycyyrrhizic" to -- Glycyrrhizic --.

Signed and Sealed this

Twenty-seventh Day of August, 2002

Attest:

Attesting Officer

JAMES E. ROGAN
*Director of the United States Patent and Trademark Office*